United States Patent
Khanuja et al.

(10) Patent No.: US 7,473,768 B2
(45) Date of Patent: Jan. 6, 2009

(54) PRIMERS AND A SCREENING METHOD FOR IDENTIFICATION OF ARTEMISININ PRODUCING PLANTS

(75) Inventors: Suman Preet Singh Khanuja, Lucknow (IN); Shilpi Paul, Lucknow (IN); Ajit Kumar Shasany, Lucknow (IN); Mahendra Pandurang Darokar, Lucknow (IN); Ashutosh Kumar Shukla, Lucknow (IN); Madan Mohan Gupta, Lucknow (IN); Anuruddha Kumar, Lucknow (IN)

(73) Assignee: Council of Scientific & Industrial Research, New Delhi (IN)

(*) Notice: Subject to any disclaimer, the term of this patent is extended or adjusted under 35 U.S.C. 154(b) by 289 days.

(21) Appl. No.: 10/813,160

(22) Filed: Mar. 31, 2004

(65) Prior Publication Data

US 2005/0142564 A1    Jun. 30, 2005

Related U.S. Application Data

(63) Continuation of application No. PCT/IN03/00404, filed on Dec. 29, 2003.

(51) Int. Cl.
*C07H 21/04* (2006.01)
*C12Q 1/68* (2006.01)

(52) U.S. Cl. .................. 536/23.1; 536/24.3; 536/24.33; 435/6; 435/91.1; 435/91.2

(58) Field of Classification Search ....................... None
See application file for complete search history.

(56) References Cited

OTHER PUBLICATIONS

Liu et al., "Artemisinin: current state adn perspectives for biotechnological production of an antimalarial drug." Appl Microbiol. Biotechnol. vol. 72, pp. 11-20. 2006.*

* cited by examiner

*Primary Examiner*—Jeanine A Goldberg
(74) *Attorney, Agent, or Firm*—Sughrue Mion, PLLC

(57) ABSTRACT

The present invention relates to a pair of primers with forward primer of SEQ ID NO. 1 having sequence of CCAAGCTTGCTGAACGCATCGG, and reverse primer of SEQ ID No. 2 having sequence of CCAAGCTTGCCACGCAGGATTATC, and a screening method for early identification of plants *Artemisia annua* having high content of artemisinin and thereby helping generation of plant population with further high content of artemisinin.

7 Claims, No Drawings

SEQUENCE LISTING

```
<160> NUMBER OF SEQ ID NOS: 23

<210> SEQ ID NO 1
<211> LENGTH: 22
<212> TYPE: DNA
<213> ORGANISM: Artificial Sequence
<220> FEATURE:
<223> OTHER INFORMATION: PCR primer

<400> SEQUENCE: 1
ccaagcttgc tgaacgcatc gg                                    22

<210> SEQ ID NO 2
<211> LENGTH: 24
<212> TYPE: DNA
<213> ORGANISM: Artificial Sequence
<220> FEATURE:
<223> OTHER INFORMATION: PCR primer

<400> SEQUENCE: 2
ccaagcttgc cacgcaggat tatc                                  24

<210> SEQ ID NO 3
<211> LENGTH: 932
<212> TYPE: DNA
<213> ORGANISM: Artemisia annua

<400> SEQUENCE: 3
aagcttgctg aacgcatcgg tgttactgcc gcagcccgtg aactcagcct gtatgaatca    60
```

-continued

| | |
|---|---|
| caactctaca actggcgcag taaacagcaa aatcagcaga cgtcttctga acgtgaactg | 120 |
| gagatgtcta ccgagattgc acgtctcaaa cgccagctgg cagaacggga tgaagagctg | 180 |
| gctatcctcc aaaaggccgc gacatacttc gcgaagcgcc tgaaatgaag tatgtcttta | 240 |
| ttgaaaaaca tcaggctgag ttcagcatca aagcaatgtg ccgcgtgctc cgggtggccc | 300 |
| gcagcggctg gtatacgtgg gtgtcagcgg cggacaagga taagcccgcg taagcagttc | 360 |
| cgccaacact gcacaggggg ttgtctcgcg ggttttaccc cgggtcaaac aagcgttacc | 420 |
| ggtgccccac gcttgaccgg atgacctgcg gtgctcaggg ttacccttta acgtaaaaaa | 480 |
| cccgtggcgg caagcttgcc cggtcaggga ctgaaggcaa aggcctcccg gaagttcagc | 540 |
| ccggtcagct accgcggcac acgggcctgc ctgtgtcaga aaatctgttg gagcaggatt | 600 |
| tttacgccca gtggcccgaa ccagaagtgg gcaggagaca tcacgtactt acgtacagat | 660 |
| gaaggctggc tgtatctggc agtggtcatt gacctgtggt cacgtgccgt tattggctgg | 720 |
| tcaatgtcgc cacgcatgac ggcgcaactg gcctgcgatg ccctgcagat ggcgctgtgg | 780 |
| cggcgtaaga ggccccggaa cgttatcgtt cacacggacc gtggaggcca gtactgttca | 840 |
| gcagattatc aggcgcaact gaagcggcat aatctgcgtg gaagtatgag cgcaaaaggt | 900 |
| tgctgctacg ataatgcctg cgtggaaagc tt | 932 |

<210> SEQ ID NO 4
<211> LENGTH: 10
<212> TYPE: DNA
<213> ORGANISM: Artificial Sequence
<220> FEATURE:
<223> OTHER INFORMATION: primer MAP01

<400> SEQUENCE: 4

| | |
|---|---|
| aaatcggagc | 10 |

<210> SEQ ID NO 5
<211> LENGTH: 10
<212> TYPE: DNA
<213> ORGANISM: Artificial Sequence
<220> FEATURE:
<223> OTHER INFORMATION: primer MAP02

<400> SEQUENCE: 5

| | |
|---|---|
| gtcctactcg | 10 |

<210> SEQ ID NO 6
<211> LENGTH: 10
<212> TYPE: DNA
<213> ORGANISM: Artificial Sequence
<220> FEATURE:
<223> OTHER INFORMATION: primer MAP03

<400> SEQUENCE: 6

| | |
|---|---|
| gtccttagcg | 10 |

<210> SEQ ID NO 7
<211> LENGTH: 10
<212> TYPE: DNA
<213> ORGANISM: Artificial Sequence
<220> FEATURE:
<223> OTHER INFORMATION: primer MAP04

<400> SEQUENCE: 7

| | |
|---|---|
| tgcgcgatcg | 10 |

```
<210> SEQ ID NO 8
<211> LENGTH: 10
<212> TYPE: DNA
<213> ORGANISM: Artificial Sequence
<220> FEATURE:
<223> OTHER INFORMATION: primer MAP05

<400> SEQUENCE: 8
aacgtacgcg                                                          10

<210> SEQ ID NO 9
<211> LENGTH: 10
<212> TYPE: DNA
<213> ORGANISM: Artificial Sequence
<220> FEATURE:
<223> OTHER INFORMATION: primer MAP06

<400> SEQUENCE: 9
gcacgccgga                                                          10

<210> SEQ ID NO 10
<211> LENGTH: 10
<212> TYPE: DNA
<213> ORGANISM: Artificial Sequence
<220> FEATURE:
<223> OTHER INFORMATION: primer MAP07

<400> SEQUENCE: 10
caccctgcgc                                                          10

<210> SEQ ID NO 11
<211> LENGTH: 10
<212> TYPE: DNA
<213> ORGANISM: Artificial Sequence
<220> FEATURE:
<223> OTHER INFORMATION: primer MAP08

<400> SEQUENCE: 11
ctatcgccgc                                                          10

<210> SEQ ID NO 12
<211> LENGTH: 10
<212> TYPE: DNA
<213> ORGANISM: Artificial Sequence
<220> FEATURE:
<223> OTHER INFORMATION: primer MAP09

<400> SEQUENCE: 12
cgggatccgc                                                          10

<210> SEQ ID NO 13
<211> LENGTH: 10
<212> TYPE: DNA
<213> ORGANISM: Artificial Sequence
<220> FEATURE:
<223> OTHER INFORMATION: primer MAP10

<400> SEQUENCE: 13
gcgaattccg                                                          10

<210> SEQ ID NO 14
<211> LENGTH: 10
<212> TYPE: DNA
<213> ORGANISM: Artificial Sequence
<220> FEATURE:
<223> OTHER INFORMATION: primer MAP11
```

```
<400> SEQUENCE: 14
ccctgcaggc                                                              10

<210> SEQ ID NO 15
<211> LENGTH: 10
<212> TYPE: DNA
<213> ORGANISM: Artificial Sequence
<220> FEATURE:
<223> OTHER INFORMATION: primer MAP12

<400> SEQUENCE: 15
ccaagcttgc                                                              10

<210> SEQ ID NO 16
<211> LENGTH: 10
<212> TYPE: DNA
<213> ORGANISM: Artificial Sequence
<220> FEATURE:
<223> OTHER INFORMATION: primer MAP13

<400> SEQUENCE: 16
gtgcaatgag                                                              10

<210> SEQ ID NO 17
<211> LENGTH: 10
<212> TYPE: DNA
<213> ORGANISM: Artificial Sequence
<220> FEATURE:
<223> OTHER INFORMATION: primer MAP14

<400> SEQUENCE: 17
aggatacgtg                                                              10

<210> SEQ ID NO 18
<211> LENGTH: 10
<212> TYPE: DNA
<213> ORGANISM: Artificial Sequence
<220> FEATURE:
<223> OTHER INFORMATION: primer MAP15

<400> SEQUENCE: 18
aagatagcgg                                                              10

<210> SEQ ID NO 19
<211> LENGTH: 10
<212> TYPE: DNA
<213> ORGANISM: Artificial Sequence
<220> FEATURE:
<223> OTHER INFORMATION: primer MAP16

<400> SEQUENCE: 19
ggatctgaac                                                              10

<210> SEQ ID NO 20
<211> LENGTH: 10
<212> TYPE: DNA
<213> ORGANISM: Artificial Sequence
<220> FEATURE:
<223> OTHER INFORMATION: primer MAP17

<400> SEQUENCE: 20
ttgtctcagg                                                              10

<210> SEQ ID NO 21
<211> LENGTH: 10
```

```
<212> TYPE: DNA
<213> ORGANISM: Artificial Sequence
<220> FEATURE:
<223> OTHER INFORMATION: primer MAP18

<400> SEQUENCE: 21
catcccgaac                                                              10

<210> SEQ ID NO 22
<211> LENGTH: 10
<212> TYPE: DNA
<213> ORGANISM: Artificial Sequence
<220> FEATURE:
<223> OTHER INFORMATION: primer MAP19

<400> SEQUENCE: 22
ggactccacg                                                              10

<210> SEQ ID NO 23
<211> LENGTH: 10
<212> TYPE: DNA
<213> ORGANISM: Artificial Sequence
<220> FEATURE:
<223> OTHER INFORMATION: primer MAP20

<400> SEQUENCE: 23
agcctgacgc                                                              10
```

PRIMERS AND A SCREENING METHOD FOR IDENTIFICATION OF ARTEMISININ PRODUCING PLANTS

This application is a Continuation of PCT/IN03/00404, filed Dec. 29, 2003. The entire disclosure of the prior application, PCT/IN03/00404, is considered part of the disclosure of the accompanying application and is hereby incorporated by reference.

FIELD OF THE PRESENT INVENTION

The present invention relates to a pair of primers with forward primer of SEQ ID NO. 1 having sequence of CCAAGCTTGCTGAACGCATCGG, and reverse primer of SEQ ID No. 2 having sequence of CCAAGCTTGCCACGCAGGATTATC, and a screening method for early identification of plants *Artemisia annua* having high content of artemisinin and thereby helping generation of plant population with further high content of artemisinin.

BACKGROUND AND PRIOR ART REFERENCES OF THE INVENTION

The plant *Artemisia annua* (family: Asteraceae) produces a sesquiterpenoid lactone endoperoxide named artemisinin which is a promising antimalarial drug effective against *Plasmodium falciparum, Plasmodium vivax* at nanomolar concentration. Artemisinins are active against *Schistosoma mansoni* and *S. japonicum* in-vitro and in-vivo in experiments in animals. These schistosomes, like malarial parasites, degrade haemoglobin and produce hemozoin. These compounds are also active against *Leishmania major, Toxoplasma gondii* and *Pnenmocystic carinii* in-vitro and against *P. carinii* in-vivo. Artemisinins have immunosuppressive activity and also potential anticancer activity. For these activities, the doses of artemisinin required are substantially higher than the dose for antimalarial activities. According to Meshnick et at., (1996) (Microbiological Reviews 6: 301 . 315) the antimalarial endoperoxides including artemisinin, dihydroartemisinin and arteethers, are not likely to be useful for other therapeutic purposes except against malarial parasites.

Although artemisinin rapidly suppresses the activity of parasites like *Plasmodium vivax* and *P. falciparum*, problems with high rate of recrudescence (>10% recrudescence infections), short half life persist. Hence, there is a need to develop new drugs against quinolone resistant pathogenic bacteria. It is a known fact that clinically used antibacterial broad spectrum compounds such as quinolones which exhibit DNA gyrase activity of *Mycobacterium* sp. (causing tuberculosis), *Haemophilus* sp. and *Haemophilus influenzae* are gradually becoming ineffective due to the occurrence of mutatious in gyrase genes and their natural selection under continuous use of such drug.

The compound α arteether developed as antimalarial drugs by Central Drug Research Institute (CDRI), Lucknow, India and Central Institute of Medicinal & Aromatic Plants (CIMAP), Lucknow, India, after phase II clinical trial is a stable derivative of artemisinin. Earlier we have found a novel property of α-arteether as being effective against the gyrA mutant strains of *E. coli* but ineffective against wild type strains (U.S. Pat. No. 6,127,405). Also we have developed a strategic and novel composition comprising α arteether and nalidixic acid or quinolone drugs which is useful as an advanced generation drug to counter the resistance development itself and having a potential to be used in treating infectious diseases and in inhibiting the resistance developed due to mutation in the gyr A gene of bacteria, particularly in those cases where drug resistant strains are known to appear very frequently (U.S. Pat. No. 6,423,741).

In an earlier invention a method was also provided for maximization of artemisinin yield of the plant *Artemisia annua*, said method comprising sowing seeds of *Artemisia annua* plant on raised bed nursery during second and third week of December and maintaining the moisture throughout; transplanting seedlings thus obtained bearing at least 5-15 leaves into the main field fertilized with fertilizer, preferably NPK @ 80,40,40 kg/ha to achieve a population density of 50,000 to 200,000 per ha followed by light irrigation in the second week of March and irrigation every fortnight thereafter; harvesting the crop four times by cutting the plant tops leaving 75-100 cm part of plant for further regeneration, the said harvests are performed in a manner that the first harvest is done in fourth week of May, second harvest in third week of July, third harvest in second week of September and fourth harvest in third week of October of each year; and at each harvesting time care is taken to care at least one green branch, and extracting artemisinin from the plant tissue immediately after each harvest. (U.S. Pat. No. 6,393,763).

Considering the high value of the chemical artemisinin for use in derivatization to different semisynthetic product of immence importance the need of the hour is to still increase the yield. Agronomic practices and scheduling of the harvest timings to obtain higher biomass yield do not take into account the genotypes as all the plants are harvested together. Since the plant *Artemisia annua* is highly cross pollinated like the members of family Asteraceae the chemical character like 'artemisinin content' seggregate like any other phenotypic characters as multigenic characters always segregate in the progeny population. Due to this all the progeny plants of the high artemisinin containing plant may not yield same amount of the chemical. Some will be high, some medium and some very low.

Considering the problem of identification of the high artemisinin containing plant genotypes at the nursery stage, to discard the low artemisinin genotypes for the purpose of planting only those genotypes which could produce high amount of artemisinin during maturity in the main field a systematic approach for identification of DNA marker was launched. In this process the marker was identified which could differentiate the high artemisinin genotypes from low artemisinin genotypes at the seedling stage itself. These selected seedlings showing the presence of the DNA marker then could be taken for further matting between them to generate plants produce highest biomass as well as higher artemisinin.

OBJECTS OF THE PRESENT INVENTION

The main object of the present invention is to develop a pair of primers capable of identifying plants *Artemisia annua* containing high content of artemisinin.

Another object of the present invention is to develop a screening method for early identification of plants *Artemisia annua* having high content of artemisinin.

In yet another object of the present invention is to develop a method for generation of plant population with further high content of artemisinin.

Still another object of the invention is to develop a method for plants to be identified at nursery stage itself having high content of artemisinin.

Still another object of the present invention is to develop a method to identify plants having high content of artemisinin ranging between 0.5 to 1.4 w/w %.

SUMMARY OF THE PRESENT INVENTION

The present invention relates to a pair of primers with forward primer of SEQ ID NO. 1 having sequence of CCAAGCTTGCTGAACGCATCGG, and reverse primer of SEQ ID No. 2 having sequence of CCAAGCTTGCCACG-CAGGATTATC, and a screening method for early identification of plants *Artemisia annua* having high content of artemisinin and thereby helping generation of plant population with further high content of artemisinin.

DETAILED DESCRIPTION OF THE PRESENT INVENTION

The present invention relates to a pair of primers with forward primer of SEQ ID NO. 1 having sequence of CCAAGCTTGCTGAACGCATCGG, and reverse primer of SEQ ID No. 2 having sequence of CCAAGCTTGCCACG-CAGGATTATC, and a screening method for early identification of plants *Artemisia annua* having high content of artemisinin and thereby helping generation of plant population with further high content of artemisinin.

In still another embodiment of the present invention, wherein a pair of primers with forward primer of SEQ ID NO. 1 having sequence of CCAAGCTTGCTGAACGCATCGG, and reverse primer of SEQ ID No. 2 having sequence of CCAAGCTTGCCACGCAGGATTATC.

In still another embodiment of the present invention, wherein A pair of primers as claimed in claim 1, wherein the primers help identify plants *Artemisia annua* containing high content of artemisinin.

In still another embodiment of the present invention, wherein A screening method for early identification of plants *Artemisia annua* having high content of artemisinin and thereby helping generation of plant population with further high content of artemisinin, said method comprising steps of:
- isolating DNA from the plant,
- running PCR on the isolated DNA using a pair of primers of SEQ ID Nos. 1 and 2,
- identifying plants having high content of artemisinin, containing nucleotide SEQ ID No. 3, and
- crossing the identified plants to produce the next generation plants with further higher content of artemisinin.

In still another embodiment of the present invention, wherein the plants can be identified at nursery stage itself.

In still another embodiment of the present invention, wherein the high content refers to concentration of 0.4 w/w/% or more.

In still another embodiment of the present invention, wherein the plant with higher content of artemisinin ranging between 0.5 to 1.4 w/w % are produced.

In still another embodiment of the present invention, wherein the increase in the artemisinin genetic advance (GA) is about 0.4 w/w % in first four years.

In still another embodiment of the present invention, wherein the artemisinin content heritability (h) is about 80.

In still another embodiment of the present invention, wherein the method helps maintains elite genotypic population.

In still another embodiment of the present invention, wherein the invention relates to a method of developing a specific DNA marker in form of a Sequence Characterized Amplified Region (SCAR) marker genetically tagged to the high artemisinin synthesizing genotypes of the plant *Artemisia annua*. Further the invention also describes the complete unique DNA sequence present in the high artemisinin containing plants. The DNA primer sequence usable for PCR amplification of tagged DNA of the plant containing high artemisinin. Also this invention illustrates the method to screen out the low artemisinin containing genotypes of *Artemisia annua* at the nursery stage itself using the DNA primers, to grow only the high artemisinin yielding genotypes to maturity for obtaining better harvest of artemisinin. Further the invention describes the method of developing high artemisinin containing plants of *Artemisia annua* using the SCAR marker through marker-assisted breeding. The invention provides the use of DNA technology to maintain elite genotypic population in a cross-pollinated plant species.

The research on genome analysis is being taken up as a necessity to understand the genomic constitution of individuals in terms of DNA content, nature and variations etc. The data from gnome analysis are of direct relevance to molecular plant breeding in which morphological characters can be tagged to unique DNA sequences and then inheritance patterns of DNA markers can be utilized to confirm the presence of traits even before expression. Techniques are available to differentiate even similar looking individuals of a population on the basis of DNA sequence variation. Some recent important discoveries from application point of view towards genetic analysis include Restriction endonucleases mapping and Polymerised Chain Reaction for amplifying DNA sequences from traces. These discoveries have led to the means and techniques used to study the differences or uniqueness in the DNA sequences otherwise known as Polymorphism in the DNA. The tools like RAPD, AFLP, RFLP, SCAR, micro-satellite and many others were invented earlier and used in literature extensively for differentiating and marking the plants for different characters.

Development of Marker Correlating to High Content of Artemisinin in the Plant *Artemisia annua*.

Selection of Genotypes

The seeds of ten chemotypic accessions of the plant *Artemisinin annua* were collected from Kashmir and further studies were carried out in Lucknow field station. Seeds of *A. annua* were sown in pots with mixture of soil and FYM (farmyard manure) in the ratio of 1:1 and germination in glass house conditions during the month of November of the years 1998-2001. The seedlings having 10 cm height were transplanted with spacing 50 cm between rows and 30 cm between plants. The soil of experimental field was sandy loam in texture and neutral in reaction (pH 7.6). The plots were fertilized with FYM (Farm yard manure) @20 kg\ha before transplanting for obtaining optimum performance. Plots were prepared 3 m×3 m size with irrigation channels. For Hybridization, six seed lots were selected out of 10 seedlots (obtained from Kashmir in the year 1998) were transplanted in alternative rows. From the next year (1999) on wards the progeny seedlings of the chemotypically selected plants were planted again in alternate rows. All the seedlings were checked for artemisinin content after extraction. About 0.1 g dry powdered plant material was extracted in 10 ml of hexane by heating at 60° C. for 3 minutes and left for overnight at room temperature. Then extract was filtered and evaporated on water bath at 50° C. After evaporation extract was dissolved in 1 ml hexane and used in TLC. Properly (20×20 cm E-MEREK) dissolved extract was spotted in TLC plates at 1 cm apart along with standard (1 mg\ml). Spotted TLC plate was dipped in solvent (mobile phase) Hexane:Diethyl ether (1:1) Plate was dried in air and dipped in developing reagent Glacial acetic acid:conc. Sulphuric acid:Anisaldehyde (50:1: 0.5 ml) and heated at 120° C. for 10-15 minutes and then Stabilized and scanned (540 nm, visible) (Densitometer CAMAG:Switzerland). The TLC plates were scanned and the artemisinin content of individual progeny plants were quantified. From the analysis the plants producing trace(0.10% or less) artemisinin and the plants producing more than 0.4% artemisinin were selected and finally 10 plants from each category were taken for DNA analysis.

DNA Isolation and PCR Amplifications

DNA was isolated from the leaf tissue essentially according to the protocol described earlier (Khanuja SPS, Shasany AK, Darokar MP, Sushil Kumar (1999) Rapid Isolation of PCR Amplifiable DNA from the Dry and Fresh Samples of Plants Producing Large Amounts of Secondary Metabolites and Essential oils by Modified CTAB Procedure. *Plant Molecular Biologic Reporter,* 17, 74.). Polymerase chain reactions (PCRs) were carried out in 25 µl volume. A reaction tube contained 25 ng of DNA, 0.2 unit of Taq DNA polymerase, 100 µM of each dNTPs, 1.5 mM $MgCl_2$ and 5 pmol of decanucleotide primers. The amplifications were carried out using the DNA Engine thermal cycler (MJ Research, USA) using 94° C., 35° C. and 72° C. temperatures for 40 cycles (Khanuja SPS, Shasany AK, Srivastava A, Sushil Kumar (2000). Assessment of genetic relationships in *Mentha* species. *Euphytica,* 111, 121-125.). The amplified products were separated on 1.2% agarose gel containing 0.5 µg $ml^{-1}$ of ethidium bromide and photographed with Image master VDS (Pharmacia). The bands were analyzed using Image master ID elite software and the graphic phenogram of the genetic relatedness among the accessions was produced by means of UPGMA (unweighted pair group method with arithmetic average) cluster analysis. Custom-made decanucleotide primers were synthesised in the laboratory on Applied Biosystems 392 DNA-RNA Synthesizer and were designated as MAP01 to MAP20. The sequences of the primers MAP01 to MAP20 were:

| | |
|---|---|
| AAATCGGAGC, | (SEQ ID NO: 4) |
| GTCCTACTCG, | (SEQ ID NO: 5) |
| GTCCTTAGCG, | (SEQ ID NO: 6) |
| TGCGCGATCG, | (SEQ ID NO: 7) |
| AACGTACGCG, | (SEQ ID NO: 8) |
| GCACGCCGGA, | (SEQ ID NO: 9) |
| CACCCTGCGC, | (SEQ ID NO: 10) |
| CTATCGCCGC, | (SEQ ID NO: 11) |
| CGGGATCCGC, | (SEQ ID NO: 12) |
| GCGAATTCCG, | (SEQ ID NO: 13) |
| CCCTGCAGGC, | (SEQ ID NO: 14) |
| CCAAGCTTGC, | (SEQ ID NO: 15) |
| GTGCAATGAG, | (SEQ ID NO: 16) |
| AGGATACGTG, | (SEQ ID NO: 17) |
| AAGATAGCGG, | (SEQ ID NO: 18) |
| GGATCTGAAC, | (SEQ ID NO: 19) |
| TTGTCTCAGG, | (SEQ ID NO: 20) |
| CATCCCGAAC, | (SEQ ID NO: 21) |
| GGACTCCACG, | (SEQ ID NO: 22) |
| AGCCTGACGC, | (SEQ ID NO: 23) | respectively.

The other sets of primers used included kit J, O and T, each consisting of 20 random decamer primers, procured from Operon Technologies Inc., USA.

All the RAPD profiles thus generated were analyzed for bands always appearing with all the high artemisinin containing genotypes (more than 0.4%) and absent in the genotypes containing trace or no artemisinin. We could detect a band at approximately 850 base pair region amplified with the primer 5'CCAAGCTTGC3' (SEQ ID No: 15) which consistently showed its presence in the genotypes containing more than 0.4% artemisinin and absent in the genotypes with trace or no artemisinin. This finding was interesting considering the complex nature of the artemisinin biosynthetic pathway. For all other primers the amplified products showed variable positions in these genotypes and could not be correlated.

The presence of the band in the segregating populations having high artemisinin could be ascertained as the samples of 10 analyzed plants having high artemisinin were drawn from different populations. Similarly, the sample of 10 plants for trace or no artemisinin drawn from different populations could show always the absence of the band. As all the plants analyzed were from the same initial population the genes for artemisinin biosynthesis were assumed to be normal. So the presence and absence of the band could be correlated to the regulatory function associated with the expression of some of the genes associated with the biosynthetic pathway. But certainly the DNA band of about 850 base pair size could be con-elated with the biosynthesis of more than 0.4% artemisinin in *Artemisia annua*.

In the next steps the DNA fragment described earlier was eluted out from the agarose gel and (since the fragment was amplified with the primer containing Hind III restriction site) restricted with Hind III restriction enzyme (Recognition and restriction site 5'AAGCTT3'). Similarly, pBluescript II SK(+) procured from Stratagene Inc. was used to clone the fragment at the Hind III site using T4 DNA ligase enzyme available commercially. *Escherichia coli* strain DH5α, procured from Stratagene Inc again was transformed with this constructed plasmid and transformed cells were isolated on agar plates containing nutrient broth and ampicillin. All the experiments were performed according to the protocol Sambrook et al (1988). This fragment was sequenced completely with the help of M13 forward and T3 reverse primer (the sequence sites are present in the plasmid pBluescript II SK(+) and the nucleotide sequence is given below of

```
AAGCTTGCTG AACGCATCGG TGTTACTGCC GCAGCCCGTG AACTCAGCCT  SEQ ID NO. 3

GTATGAATCA CAACTCTACA ACTGGCGCAG TAAACAGCAA AATCAGCAGA

CGTCTTCTGA ACGTGAACTG GAGATGTCTA CCGAGATTGC ACGTCTCAAA
```

```
-continued
CGCCAGCTGG CAGAACGGGA TGAAGAGCTG GCTATCCTCC AAAAGGCCGC

GACATACTTC GCGAAGCGCC TGAAATGAAG TATGTCTTTA TTGAAAAACA

TCAGGCTGAG TTCAGCATCA AAGCAATGTG CCGCGTGCTC CGGGTGGCCC

GCAGCGGCTG GTATACGTGG GTGTCAGCGG CGGACAAGGA TAAGCCCGCG

TAAGCAGTTC CGCCAACACT GCACAGGGGG TTGTCTCGCG GGTTTTACCC

CGGGTCAAAC AAGCGTTACC GGTGCCCCAC GCTTGACCGG ATGACCTGCG

GTGCTCAGGG TTACCCTTTA ACGTAAAAAA CCCGTGGCGG CAAGCTTGCC

CGGTCAGGGA CTGAAGGCAA AGGCCTCCCG GAAGTTCAGC CCGGTCAGCT

ACCGCGGCAC ACGGGCCTGC CTGTGTCAGA AAATCTGTTG GAGCAGGATT

TTTACGCCCA GTGGCCCGAA CCAGAAGTGG GCAGGAGACA TCACGTACTT

ACGTACAGAT GAAGGCTGGC TGTATCTGGC AGTGGTCATT GACCTGTGGT

CACGTGCCGT TATTGGCTGG TCAATGTCGC CACGCATGAC GGCGCAACTG

GCCTGCGATG CCCTGCAGAT GGCGCTGTGG CGGCGTAAGA GGCCCCGGAA

CGTTATCGTT CACACGGACC GTGGAGGCCA GTACTGTTCA GCAGATTATC

AGGCGCAACT GAAGCGGCAT AATCTGCGTG GAAGTATGAG CGCAAAAGGT

TGCTGCTACG ATAATGCCTG CGTGGAAAGC TT.
```

Based on the sequence at the ends forward and reverse primers were synthesized with the sequence

```
Forward Primer
5'CCAAGCTTGCTGAACGCATCGG3'      (SEQ ID NO. 1)

Reverse primer
5'CCAAGCTTGCCACGCAGGCATTATC3'   (SEQ ID NO. 2)
```

These sequences were used to amplify the genomic DNA of *Artemisia annula* (both high content of artemisinin and low content of artemisinin). The plant genomic DNA with high artemisinin content could generate a band of 936 bp where as in plants containing low amount of artemisinin the absence of the band was conspicuous.

Use of the Marker to Generate a Population of Plants with High Artemisinin Content.

In the first year polycross nursery was designed with alternate male and female line choosen among the seedlots. These plants were randomly picked up from the nursery raised from the 6 selected seed lots. The plants, which were designated as female (270 plants), were analyzed for artemisinin content, which were selected for further experimentation. Seed sample were collected from these selected plants (13 in number) containing high amount of artemisin (0.15 to 0.20%) and planted again in a polycross nursery in the second year. Next year 180 plants were analyzed for artemisinin content and 13 plants containing 0.45 to 0.50% artemisinin were selected for planting in the third year. At this point 10 plants with more than 0.4% artemisinin and 10 plants containing trace amount artemisinin were taken for DNA isolation to develop SCAR marker as described previously. The SCAR marker was used to select plants from the nursery raised from the seeds selected 13 seedlots, and 12 plants from each seedlots showing the presence of SCAR marker were selected for random crossing among the plants in the third year. Randomly plants were analyzed for artemisinin content and among 150 plants analyzed 20 plants having artemisinin 0.8 to 1.0% were selected for next year (fourth year) planting. The seeds from these plants were grown in the nursery and 12 SCAR positive plants from each seed lot were grown randomly to facilitate cross pollination. From these 200 plants were analysed for artemisinin content and 11 plants were selected having 1.0 to 1.16% artemisinin content. Simultaneously, increase in the mean artemisinin content of the plants analysed every year were calculated.

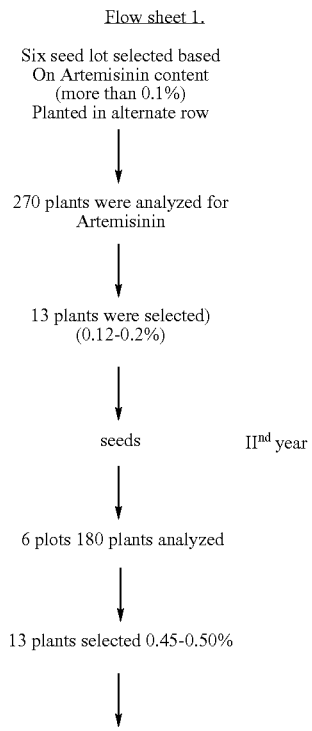

Flow sheet 1.

Six seed lot selected based
On Artemisinin content
(more than 0.1%)
Planted in alternate row

↓

270 plants were analyzed for
Artemisinin

↓

13 plants were selected)
(0.12-0.2%)

↓ seeds       II$^{nd}$ year

↓

6 plots 180 plants analyzed

↓

13 plants selected 0.45-0.50%

↓

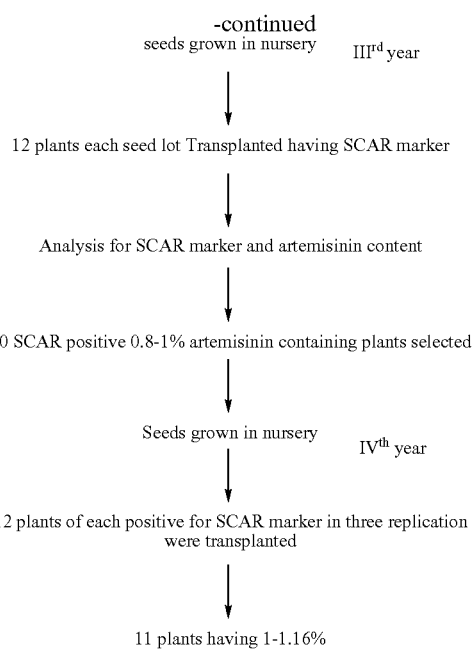

Genetic Advancement

The key metabolite synthesis (Artemisinin content) was studied for genetic advancement which showed an upward trend beginning with 17.33% increase in the mean artemisinin content for the first year, crossing 50% in second year, 60% in third year and remaining at 42.06% in fourth year. The advancement in artemisinin content was calculated as per Singe and Chaudhary (1977) (Singh R K and Chaudhary B D (1977). Biometrical methods in quantitative genetic analysis. Kalyani Publications, New Delhi.

GA: Genetic advance=$i \times h^2 \times \sigma p$
i=i is the standardized selection differential
σp phenotypic standard deviation
$h^2$=heritability

TABLE

| S. No. | Traits | I year | II year | III year | IV year |
|---|---|---|---|---|---|
| 1 | Artemisinin GA | 0.013 | 0.167 | 0.36 | 0.39 |
|  | Content(%) GA(% of x) | 17.33 | 53.87 | 60.00 | 52.06 |
|  | h (b) | 18 | 52 | 76 | 70 |

One of the object of the present invention was to develop a marker system to be used in breeding *Artemisia annua* plant for high artemisinin content. The marker was developed and described as the unique sequence which appear in plants containing high amount of artemisinin (0.4% or more). The Indian genotypes of *Artemisia annua* found in wild have low content of artemisinin. This marker system can distinguish plant tending to synthesize high amount of artemisinin when the biosynthetic system of the plant is functional (i.e. structural genes). Other objective of the invention was to generate a breeding and selection method using the marker assisted breeding to increase the content of artemisinin in the plants. From 0.1% artemisinin content, the plants were improved to 1.2% using the protocol and the marker system.

The invention claimed is:

1. A pair of primers consisting of a forward and a reverse primer wherein the forward primer consists of SEQ ID NO. 1 and the reverse primer consists of SEQ ID NO. 2.

2. A method for identifying *Artemisia annua* plants that contain more than 0.4 w/w/ % artemisinin, comprising
   obtaining DNA from said *Artemisia annua* plant
   amplifying said DNA by polymerase chain reaction using the pair of primers of claim 1
   identifying *Artemisia annua* plants containing more than 0.4 w/w/ % artemisinin.

3. A method for increasing the yield of artemisinin production in progeny *Artemisia annua* plants, said method comprising the steps of:
   a. obtaining DNA from *Artemisia annua* plants,
   b. amplifying said DNA by polymerase chain reaction using the pair of primers of claim 1,
   c. identifying *Artemisia annua* plants containing more than 0.4 w/w/ % artemisinin
   d. crossing *Artemisia annua* plants containing more than 0.4 w/w/ % artemisinin to generate *Artemisia annua* progeny plants.

4. The method of claim 3, wherein said *Artemisia annua* plants containing more than 0.4 w/w/ % artemisinin are identified at nursery-stage.

5. The method of claim 3, wherein *Artemisia annua* progeny plants containing 0.8-1.16 w/w % artemisinin are produced.

6. The method of claim 3, wherein an increase in artemisinin genetic advance (GA) of about 0.4 w/w % occurs within four years.

7. The method of claim 3, wherein artemisinin content heritability (h) is about 80.

* * * * *